United States Patent [19]
Consolazio et al.

[11] 4,348,424
[45] Sep. 7, 1982

[54] SPRAYABLE PLANT CARE COMPOSITION

[75] Inventors: George A. Consolazio, Burlington; James A. Sheppard, Newburyport; Benjamin E. Laramee, East Pepperell, all of Mass.

[73] Assignee: General Foods Corporation, White Plains, N.Y.

[21] Appl. No.: 248,083

[22] Filed: Mar. 27, 1981

[51] Int. Cl.$^3$ .................. A01G 5/06; C05B 17/00
[52] U.S. Cl. .......................... 427/4; 71/19; 71/15; 71/29; 71/64.1
[58] Field of Search ............. 47/DIG. 11; 71/DIG. 1, 71/64.10, 64.8, 64.11, 29, 204, 19, 22, 15, 64.1, 64.09; 427/4

[56] References Cited
U.S. PATENT DOCUMENTS 2,128,973  9/1938  Tisdale .................... 47/DIG. 11
3,157,964  11/1964  Ferguson ........................ 427/4
3,847,641  11/1974  Cushman ................. 47/DIG. 11

FOREIGN PATENT DOCUMENTS 499858  3/1976  U.S.S.R. ............... 47/DIG. 11

Primary Examiner—Sam Silverberg
Attorney, Agent, or Firm—Thomas V. Sullivan; Daniel J. Donovan; Bruno P. Struzzi

[57] ABSTRACT

The invention provides a sprayable plant care composition which, in its preferred aspects, comprises a continuous aqueous phase comprising gelatin hydrolysate, urea, dissolved phosphorus and potassium salts, and an amount of preservative effective to prevent microbial growth in the composition; a dispersed phase comprising orange peel wax and glycerol as a diluent for the wax; and an emulsifier comprising polyoxyethylene (20) sorbitan monostearate in an amount effective to provide a stable emulsion and provide a cleansing action when the composition is applied to the foliage of a plant. When applied as a spray to plant leaf surfaces, the composition produces an attractive shine and an appealing aroma, provides plant nutrients absorbable by the leaf, and serves as an effective rinse to cleanse the leaf.

9 Claims, No Drawings

SPRAYABLE PLANT CARE COMPOSITION

DESCRIPTION

1. Technical Field

The invention relates to plant care compositions; and particularly, to compositions which can be sprayed onto the foliage of plants to enhance their beauty and growth.

The proper care and maintenance of plants, particularly the broad-leaved varieties employed indoors for decorative purposes, is to some people a pleasure and to others a mystery. There are currently a wide variety of commercial products promoted on the basis that they will simplify the successful growth of beautiful plants. Some of these products can be sprayed onto the foliage of broad-leaved plants to provide a highly polished surface. These products, however, do not actually beautify the plants through encouraging the natural growth process. They simply provide a glossy surface to the foliage. Despite this initially glossy surface, dust and water-soluble materials collect upon the surface of the leaves, and because proper maintenance of the plants calls for misting the leaves with water or an aqueous solution containing other plant treating agents, the shiny surfaces often become dulled and water spotted. This spotting is aggravated where the aqueous solution contains soluble materials such as nutrients which remain upon the shiny leaves upon drying. This then requires a repeated, separate treatment with the gloss composition. The repeated alternate treatments with the various sprays ultimately results in the buildup of a film which to some extent dulls the natural color of the leaves.

2. Background Art

U.S. Pat. No. 3,847,641 to Cushman et al. is directed to a composition for use in dry climates which controls the transpiration in plants. In many areas, the shortage of natural ground water threatens the survival of plants unless a coating is applied to the foliage to prevent loss of moisture from the leaves. Cushman et al. teach spraying the plant surface with a wax emulsion composition consisting essentially of paraffin wax, petrolatum, and at least one emulsifier in an aqueous vehicle. Compositions can also contain protective colloids such as natural gums, gelatin, casein and cellulose derivatives. These materials in combination with the emulsifiers are said to result in improved storage stability of the emulsion by avoiding separation of the aqueous phase. Despite the known utility of gelatin as a protective colloid and also as a plant food when applied to the soil, the gelatin in this case would, upon drying, become brittle, thereby affecting the physical properties of the coating and remain unavailable for use as a source of nutrients for the plant.

In U.S. Pat. No. 3,157,964 to Ferguson et al. there is disclosed a water-retentive treating composition for application to plants. This composition is applied as a high viscosity liquid by spraying to form a thick film. The film is described as comprising a polyhydric alcohol humectant and an ammonium salt of an addition polymer of an alpha, beta-ethylenically unsaturated carboxylic acid. It is disclosed that the film can also contain a dissolved polyvalent metal compound, a fungicide, a source of oxygen, a preservative, a plant nutrient, a plant hormone or any mixture of these. While it is indicated that the thick film enhances the clarity and gloss of various plants, the highly viscous material would have to be applied with care in indoor situations to prevent damage to surrounding areas, especially where a disclosed feature of the composition is that it resists removal by water.

Other patents, such as U.S. Pat. No. 2,770,538 and U.S. Pat. No. 2,869,996 to Vierling, discuss liquid fertilizers suitable for spraying onto plant foliage. Both of these patents describe compositions containing a wetting or surface-active agent to promote the absorption of the nutrients by the plant. These compositions, however, do not enhance the appearance of the plants by creating a glossy or shiny surface on the leaves. In fact, application of these materials to the leaves can result in spotting and generally dulling of the leaf surfaces.

Other liquid fertilizer materials are intended for application to the soil and not for direct application to the leaves. Among these is U.S. Pat. No. 3,192,030 to Mills et al. which discloses the use of an emulsion composition comprising an aqueous phase containing plant nutrients, a discontinuous oil phase comprising a wax and an organic solvent, and an emulsifying agent. Application of this composition to the soil by spraying provides a slow release of nutrients through the roots of the plant.

DISCLOSURE OF INVENTION

The present invention provides an improved plant care spray composition which fosters plant beauty by providing the nutrients necessary for vigorous growth while at the same time cleaning the leaves of dust and soluble materials and depositing a thin film of a glossy material which enhances the natural coloration of the plant. Also provided is a plant care regimen which includes the periodic application of the composition of the invention to a plant by spraying.

The composition according to the invention comprises an emulsion containing: a continuous aqueous phase comprising gelatin hydrolysate, urea, dissolved phosphorus and potassium salts, and an amount of preservative effective to prevent microbial growth in the composition; a dispersed phase comprising plant wax and a diluent for the wax; and an emulsifier in an amount effective to provide a stable emulsion and provide a cleaning action when the composition is applied to the foliage of a plant.

The regimen for plant care according to the invention comprises: spraying a plant with the composition as defined above in an amount sufficient to fully wet the foliage and cause runoff of a portion of the applied composition; permitting the composition to dry; and repeating the spraying and drying at regular intervals of time effective to maintain a supply of nutrient for the plant.

Best Mode for Carrying Out the Invention

The following detailed presentation will discuss the invention in its preferred aspects and will include the identification of preferred components of the composition. It is to be understood, however, that materials which function fully equivalently with those specifically identified, can be employed in place of those specifically identified.

It is important for the composition to be in the form of a stable oil-in-water emulsion to assure consistent properties enabling uniform spraying and application to the plant being treated. Thus, a suitable emulsifier must be present in an amount effective to provide a stable emulsion. The emulsifier should also be selected in terms of its composition and employed in an amount effective to provide a cleansing action when applied to the plant. Dust, residues from other plant sprays, plant secretions, and the like can collect on the surface of plant foliage. To achieve the greatest beauty, and therefore the greatest enjoyment from the plant, it is important to remove these materials. It is an advantage of the present invention that these materials can be removed simultaneously with the feeding and glossing of the foliage.

Among the suitable emulsifiers are the polysorbates, particularly polysorbate 60, polysorbate 65, and polysorbate 80. Polysorbate 60 is otherwise known as polyoxyethylene (20) sorbitan monostearate and is commercially available under the trademarks Tween 60 from ICI-Atlas, Drewpone 60 from PVO International Inc., Durfax 60 from SCM Corporation, and GYSPS-20 from Glyco, Inc. Polysorbate 65 is otherwise known as polyoxyethylene (20) sorbitan tristearate and is commercially available under the trademarks Tween 65, Drewpone 65, Durfax 65, and GYSPT-20. Polysorbate 80 is technically known as polyoxyethylene (20) sorbitan monooleate and is commercially available under the trademarks Tween 80, Drewpone 80, Durfax 80 and GYSPO-20. These emulsifiers are all hydrophilic; however, it is not critical to employ emulsifiers having equivalently high HLB values. Any emulsifier which will be effective for the stated purposes in reasonable amounts can be employed.

The emulsifier will typically be employed in an amount of from about 0.01 to about 1.0% based upon the total weight of the composition. A specific amount will, of course, depend upon the total concentration of the oily phase materials and the total amount of the water in the composition. The emulsifier must be present in an amount effective to provide a stable emulsion of the oil phase within the aqueous phase and must also be present in an amount sufficient to provide a washing action when the composition is applied to a plant. According to the more preferred aspects of the invention, the preferred emulsifier systems will be employed in amounts within the range of from about 0.05 to about 0.2% based upon the total weight of the composition and from about 5 to 100% of the weight of the oily phase.

The oily phase of the composition will comprise at least a plant wax and a diluent for the wax. Among the various waxes which can be employed are orange peel wax, other citrus peel waxes, citrus seed waxes, carnauba wax, ouricury wax and candelilla wax. Of these, the orange peel wax is presently considered the most preferred; in part due to its highly effective glossing action in the preferred composition, and in part due to its desirable scent. Unlike adding scents to waxes not containing the scent naturally, the orange peel wax maintains a desirable level of scent uniformly over an extended period of time.

The exact amount in which the wax is employed is not critical so long as it is present in an amount effective to provide a glossy surface to the plant by spraying an amount of the composition on the plant to fully wet the surface. According to the preferred aspects of the invention, the wax will be present in an amount of from about 0.05 to about 1% of the total weight of the composition. Particularly preferred levels will be within the range of from about 0.1 to about 0.5% on the same basis.

It is important to employ a diluent for the wax to give it a liquid consistency at ordinary temperatures of application, typically above 0° C. Among the suitable diluents are various polyhydric alcohols such as glycerol, 1,2-propanediol, 1,3-butanediol and polyethylene glycols having molecular weights ranging from 200 to 4000 and commercially available under the trademark Carbowax from Union Carbide Corporation. Of these, glycerol is presently the most preferred in combination with the orange peel wax. However, it is recognized that 1,2-propanediol and 1,3-butanediol have limited antimicrobial properties in addition to their enhancement of the spreading properties of the wax over the surface of the leaves. The amount of diluent is fairly closely controlled by the type and the amount of the wax, and should be present in an amount effective to enable the particular wax employed to spread into a uniform, thin layer over the plant surface upon drying after a uniform coating has been sprayed thereto. Typically, the diluent will be present in proportion to the wax to provide a weight ratio of wax to diluent of within the range of from about 1:1 to about 1:10. Preferably, and especially when employing the preferred orange peel wax in the glycerol, the weight ratio of the wax to the diluent will be within the range of from about 2:3 to 1:4.

Another principal feature of the present invention is the use of gelatin hydrolysate in the aqueous phase to supply nutrient directly through the plant foliage to which it is applied. The gelatin hydrolysate, having a Bloom of 0, unlike unhydrolyzed gelatin, having a Bloom of from about 50 to about 300, can be absorbed more readily through the foliage. The Bloom is measured and tested by a standard method for Bloom measurement; cf., "Standard Methods for the Sampling and Testing of Gelatins," Bulletin published by Gelatin Manufacturers Institute of America, Inc., New York, N.Y. Moreover, the gelatin hydrolysate maintains the uniform glossy appearance provided by the composition, and is flexible within the coating remaining after the water has dried from the composition. Thus, the gelatin hydrolysate does not result in a cracking or crazing of the coating as would be the case if unhydrolyzed gelatin were employed.

While gelatin hydrolysate prepared by any method effective to provide a sufficiently low molecular weight material to enable absorption by the plant foliage would be suitable, it is preferred that the gelatin hydrolysate be reduced in molecular size such that a 6% solution is non-gelling. Preferably, the gelatin hydrolysate is prepared by hydrolyzing a typical commercial grade of gelatin, derived from the skin, while connective tissues and bones of various animals, having a Bloom value of from about 50 to about 300 by contacting it with a proteolytic enzyme, typically bromelain, at a temperature of from about 30° to about 65° C., preferably at a temperature of from about 40° to about 45° C., at a pH of about 4 to about 9 for a time of from about 30 to about 60 minutes. Other proteolytic enzymes such as papain or ficin may also be employed under slightly varied conditions. Alternatively, acid or alkaline hydrolysis can be employed; however, these are not preferred because the hydrolysis has to be conducted at higher temperatures resulting in more highly colored products. Also, collagen itself can be directly broken down to the hydrolysate following generally recognized procedures.

In addition to its function of providing soluble nutrients to the plant, the gelatin hydrolysate also serves to form a film and thus aids in the formation of the glossy appearance on the leaves. Accordingly, the gelatin hydrolysate will be employed in amounts higher than would be typically employed if supplying nutrients to the plant were its only function, and it will preferably be employed in an amount of from about 0.5 to 5.0%. Concentrations below this range will be effective for providing proper nutrient to the plant; however, they will not provide the desirable film forming properties obtained according to the present invention. Levels in excess of 5% would generally not be employed because they would, at these high levels, tend to diminish the glossy appearance of the film. Particularly preferred levels will be within the range of from 1 to 3% based upon the total weight of the composition, especially when the preferred combination of orange peel wax and glycerine diluent are employed at the preferred concentrations.

The aqueous phase of the emulsion composition of the present invention will also contain urea and sufficient dissolved potassium and phosphorus salts to provide a balanced plant food. Among the potassium and phosphorus salts which can be employed are ammonium phosphate, potassium phosphate, potassium nitrate, potassium chloride, potassium hydroxide, and other water-soluble salts containing these materials. Preferably, the composition of the present invention will, from among the urea and the other highly-soluble nutrients, contain a weight ratio of nitrogen:phosphoric acid ($P_2O_5$):soluble potash ($K_2O$) of from within the range of from about one part of each up to about 10 parts of any one of the other components. Preferably, the nutrients will be balanced with no one of them being greater than about 2 times the amount of any of the others. The amount of available nitrogen will, however, be increased substantially by the nitrogen available from the gelatin hydrolysate. As desired, the soluble nutrients can contain calcium, sulfur, and magnesium and various amounts of micro or trace elements such as boron, manganese, iron, zinc, molybdenum, and copper as may be desired for intensive plant growth.

Because the composition of the present invention comprises a gelatin hydrolysate which is a very good growth medium for bacteria, it is important to employ a preservative in the composition in an amount effective to prevent the microbial growth in the composition. Among the preservatives which can be employed are those of the quaternary-ammonium type, potassium sorbate and the methyl, ethyl, propyl and butyl esters of para-hydroxybenzoic acid. Among the suitable commercially available preservatives is Hyamine 3500. Typically, these preservatives will be employed in an amount of from about 0.01 to about 1.0%. In the preferred case of the commercially available Hyamine 3500 preservative, a level of about 0.05% active agent is effective.

The composition of the present invention is preferably prepared for commercial use in its liquid form, containing the total amount of water required for application, typically from about 90 to about 98% of the composition. It is possible, however, to prepare a concentrated emulsion for subsequent dilution to the desired strength. This would have the advantage that smaller containers could be used and the shipping would be less costly. On the other hand, it would be disadvantageous because of the inconvenience of the mixing step. Similarly, it is within the skill of the art to provide an emulsion which is stable enough for drying such as by spray drying, and packaging the composition in dry form for later redispersion in water.

The composition of the present invention can be employed to enhance the growth and appearance of a wide number of plants. Among these are the following: Prayer Plant, Rubber Tree, Peperomia, Orchid, Dragon Tree, Philodendron, *Philodendron sellocitum,* Dumb Cane, Umbrella Plant, *Epidermiun aureum, Marantha leuconeura, Ficus diversifolia/elastica, Peperonia obtusifolia* and *capenatum,* Purpofilia sp. Saintpaulia, *Paphiopedilum maudiae, Dracena marginata,* Diffenbachia, Schefflera, Zerbra, Aucuba, Croton, *Aphelandra squarrosa,* Gold Dust Tree, *Codiaeum variegatum pictum, Schefflera actionphylla,* Diffenbachia, and Plectranthus.

Unlike the prior art plant gloss compositions and those intended for protecting the plants from extemes in climatic conditions, the composition of the present invention is particularly adapted to providing a regimen for plant care which will maintain the growth and attractiveness of a plant over an extended period of time. In its broad aspects, the regimen comprises spraying a plant with the composition according to the invention in an amount sufficient to fully wet the foliage and cause runoff of a portion of the applied composition; permitting the composition to dry; and repeating the spraying at regular intervals of time to maintain a supply of nutrients for the plant. It is important that the composition be applied in an amount sufficient to permit at least some runoff because this enables the composition to wash water-soluble and water-dispersable materials from the surfaces of the plants. Also, this assures a complete wetting of the plant with the nutrients and gloss-establishing materials. Upon drying, the coaction of the wax, its diluent, and the gelatin hydrolysate will provide a color-richening gloss which will enhance the beauty of the plant.

The particular type of plant, the particular conditions of heat and light under which the plant is maintained, and other environmental factors will determine the exact period of time between applications. Typically, however, for most house plants, it is desirable to repeat the spraying application at time intervals of from about 1 week to about 2 months. Preferred time intervals would be within the range of from about 2 weeks to about 6 weeks. The level of nutrients within the composition may be adjusted for particular types and varieties of plants if desired so that a more exact regimen can be specified on a container label. The composition can be sprayed by any suitable spraying device of the type which are now typically employed for these purposes. If desired, the composition can be packaged in a hand-actuated or aerosol spray container.

The following example is presented for the purpose of further illustrating and explaining the present invention and is not to be taken as limiting in any regard. Unless otherwise indicated, all parts and percentages are by weight.

EXAMPLE

This example describes the preparation of a plant care composition according to the invention and describes its use in comparison with the treatment of a broad leaf plant by conventional periodic misting with plain tap water.

The composition contains the following ingredients:

| Ingredients | Weight % |
| --- | --- |
| Orange peel wax | 0.25 |
| Polysorbate 60 (Tween 60) | 0.13 |
| Glycerine | 2.12 |
| Urea | 0.0713 |
| Ammonium phosphate | 0.0780 |
| Potassium phosphate | 0.0014 |
| Potassium nitrate | 0.0856 |
| Aqueous solution of gelatin hydrolysate at 55% solids concentration | 3.64 |
| Aqueous solution of a bacteriocide, (Hyamine 3500) at 10% concentration | 0.51 |
| Water | 93.1137 |

The composition is prepared by combining the orange peel wax, polysorbate 60, glycerine and gelatin hydrolysate in a suitable vessel, heating the mixture and holding it at 80° C. until a thick emulsion is formed. The emulsion is then added to a water solution of the urea, phosphates, nitrate and preservative.

The above composition is sprayed on one half of the leaves of a broad leaf variegated house plant in sufficient quantity to rinse the surface; and the other half of the leaves are sprayed with a like amount of water. Once the leaves are dry, a comparison shows the conventionally treated leaves to be water-spotted and dull. The natural variegation is not shown on these leaves in the best contrast. On the other hand, the treated leaves are pleasantly glossy, with the dual colors in pleasing contrast, and showing no sign of water spotting. Moreover, the leaves treated according to the invention emanate an enjoyable fragrance.

When a similar plant is treated with the composition of the invention prepared above, on a regimen calling for spraying every three weeks, the plant so treated for a total of ten months shows increased growth over the control; the treated leaves are more shiny and their color is more pronounced than those of the control.

The above description has been for the purpose of teaching the person skilled in the art how to practice the invention. It has not been our intention to describe each and every obvious modification of the invention which will become apparent upon reading the description. It is intended, however, to include all such modifications and variations within the scope of the invention which is defined in the following claims.

We claim:

1. A sprayable plant care composition comprising an emulsion containing: a continuous aqueous phase comprising gelatin hydrolysate, urea, dissolved phosphorus and potassium salts, and an amount of preservative effective to prevent microbial growth in the composition; a dispersed phase comprising plant wax and a diluent for the wax; and an emulsifier in an amount effective to provide a stable emulsion and provide a cleaning action when the composition is applied to the foliage of a plant.

2. A composition according to claim 1 wherein the wax comprises orange peel wax.

3. A composition according to claim 1 wherein the diluent comprises glycerol.

4. A composition according to claim 1 wherein the emulsifier comprises polyoxyethylene (20) sorbitan monostearate.

5. A composition according to claim 1 wherein the dissolved phosphorus and potassium salts comprise ammonium phosphate, potassium phosphate, and potassium nitrate.

6. A composition according to claim 5 wherein the wax comprises orange peel wax.

7. A composition according to claim 6 wherein the wax diluent comprises glycerol.

8. A composition according to claim 7 wherein the emulsifier comprises polyoxyethylene (20) sorbitan monostearate.

9. A plant care regimen comprising: spraying a plant with a composition according to either of claims 1 or 8 in an amount sufficient to fully wet the foliage and cause runoff of a portion of the applied composition; permitting the composition to dry; and repeating the spraying at regular intervals of time to maintain a supply of nutrients for the plant.

* * * * *